(12) United States Patent
Den Boef (10) Patent No.: US 8,031,337 B2
(45) Date of Patent: Oct. 4, 2011

(54) ANGULARLY RESOLVED SCATTEROMETER

(75) Inventor: Arie Jeffrey Den Boef, Waalre (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 12/493,606

(22) Filed: Jun. 29, 2009

(65) Prior Publication Data

US 2009/0262366 A1 Oct. 22, 2009

Related U.S. Application Data

(62) Division of application No. 11/731,025, filed on Mar. 30, 2007, now Pat. No. 7,570,358.

(51) Int. Cl.
*G01J 3/28* (2006.01)
*G01J 3/06* (2006.01)

(52) U.S. Cl. .......... 356/326; 356/301; 250/339.02; 250/458.1; 359/308

(58) Field of Classification Search ......... 356/300–301, 356/326; 250/234, 201.3, 339.02, 458.1; 359/368–398
See application file for complete search history.

(56) References Cited

U.S. PATENT DOCUMENTS

| | | | |
|---|---|---|---|
| 4,771,629 A * | 9/1988 | Carlson et al. | 73/23.35 |
| 5,111,038 A * | 5/1992 | Taylor et al. | 250/225 |
| 5,216,484 A | 6/1993 | Chao et al. | |
| 5,357,097 A | 10/1994 | Shiozawa et al. | |
| 5,377,003 A | 12/1994 | Lewis et al. | |
| 5,410,371 A * | 4/1995 | Lambert | 348/769 |
| 5,438,406 A | 8/1995 | Puschell | |
| 5,475,221 A | 12/1995 | Wang | |
| 5,703,692 A | 12/1997 | McNeil et al. | |
| 5,796,512 A | 8/1998 | Wachman et al. | |
| 5,841,577 A * | 11/1998 | Wachman et al. | 359/386 |
| 5,880,838 A | 3/1999 | Marx et al. | |
| 5,963,329 A | 10/1999 | Conrad et al. | |
| 6,608,690 B2 | 8/2003 | Niu et al. | |
| 6,699,624 B2 | 3/2004 | Niu et al. | |
| 6,704,661 B1 | 3/2004 | Opsal et al. | |
| 6,721,691 B2 | 4/2004 | Bao et al. | |
| 6,738,138 B2 | 5/2004 | Wei | |
| 6,753,961 B1 | 6/2004 | Norton et al. | |
| 6,768,983 B1 | 7/2004 | Jakatdar et al. | |
| 6,772,084 B2 | 8/2004 | Bischoff et al. | |
| 6,785,638 B2 | 8/2004 | Niu et al. | |
| 6,813,034 B2 | 11/2004 | Rosencwaig et al. | |
| 6,819,426 B2 | 11/2004 | Sezginer et al. | |

(Continued)

FOREIGN PATENT DOCUMENTS

EP 1 148 390 A2 10/2001

(Continued)

OTHER PUBLICATIONS

"Acoustooptical Tunable Filter", 1996, Wolfram Research, http://scienceworld.wolfram.com/physics/AcoustoopticalTunableFilter.html.

(Continued)

*Primary Examiner* — Sang Nguyen
(74) *Attorney, Agent, or Firm* — Sterne, Kessler, Goldstein & Fox P.L.L.C.

(57) ABSTRACT

An angularly resolved scatterometer uses a broadband radiation source and an acousto-optical tunable filter to select one or more narrowband components from the broadband beam emitted by the source for use in measurements. A feedback loop can be used to control the intensity of the selected narrowband components to reduce noise.

12 Claims, 3 Drawing Sheets

U.S. PATENT DOCUMENTS

| | | |
|---|---|---|
| 6,856,408 B2 | 2/2005 | Raymond |
| 6,919,964 B2 | 7/2005 | Chu |
| 6,928,628 B2 | 8/2005 | Seligson et al. |
| 6,965,431 B2 | 11/2005 | Vo-Dinh et al. |
| 6,972,852 B2 | 12/2005 | Opsal et al. |
| 6,974,962 B2 | 12/2005 | Brill et al. |
| 6,987,572 B2 | 1/2006 | Lakkapragada et al. |
| 7,046,376 B2 | 5/2006 | Sezginer |
| 7,061,615 B1 | 6/2006 | Lowe-Webb |
| 7,061,623 B2 | 6/2006 | Davidson |
| 7,061,627 B2 | 6/2006 | Opsal et al. |
| 7,068,363 B2 | 6/2006 | Bevis et al. |
| 7,103,402 B2 | 9/2006 | Vo-Dinh |
| 7,317,531 B2 | 1/2008 | Mieher et al. |
| 7,433,040 B2 | 10/2008 | Mieher et al. |
| 7,564,557 B2 | 7/2009 | Mieher et al. |
| 7,570,358 B2 | 8/2009 | Den Boef |
| 7,663,753 B2 | 2/2010 | Mieher et al. |
| 2002/0185608 A1 | 12/2002 | Wieser |
| 2004/0119970 A1 | 6/2004 | Dusa et al. |
| 2006/0033921 A1 | 2/2006 | Den Boef et al. |
| 2006/0066855 A1 | 3/2006 | Boef et al. |
| 2006/0126074 A1 | 6/2006 | Van Der Werf et al. |
| 2006/0139592 A1 | 6/2006 | Den Boef et al. |

FOREIGN PATENT DOCUMENTS

| | | |
|---|---|---|
| EP | 1 372 040 A2 | 12/2003 |
| EP | 1 372 040 A3 | 12/2003 |
| JP | 2003-065955 A | 3/2003 |
| WO | WO 95/17662 A1 | 6/1995 |
| WO | WO 2004/053426 A1 | 6/2004 |
| WO | WO 2004/076963 A2 | 9/2004 |
| WO | WO 2004/079351 A1 | 9/2004 |

OTHER PUBLICATIONS

"Acousto-Optical Tunable Filters", Del Mar Ventures, May 4, 2004, http://www.sciner.com/Acousto-Optics/acoustooptical_tunable_filters.htm.

Fellers et al.," Acousto-Optic Tunable Filters (AOTFs)," Theory of Confocal Microspy, 2004, Olympus Corporation, Olympus Fluoview Resource Center: Acousto-Optic Tunable Filters, http://www.olympusfluoview.com/theory/aotfintro.html.

Spring et al., "Acousto-Optic Tunable Filters", Interactive Java Tutorials, May 21, 2003, Molecular Expressions: Optical Microscopy Ptimer Physics of Light and Color, http://micro.magnet.fsu.edu/primer/java/fllters/aotf/index.html.

Notice of Reasons for Rejection mailed Jul. 13, 2010 for Japanese Patent Application No. 2008-072791, 3 pgs.

English Abstract for Japanese Publication No. 2006-518942T published Aug. 17, 2006, 1 pg.

English Abstract for Japanese Publication No. 2006-509219T published Mar. 16, 2006, 1 pg.

English Abstract for Japanese Publication No. 2006-519395T published Aug. 24, 2006, 1 pg.

* cited by examiner

ANGULARLY RESOLVED SCATTEROMETER

CROSS-REFERENCE TO RELATED APPLICATION

This application is a divisional of U.S. application Ser. No. 11/731,025, filed on Mar. 30,2007 (now U.S. Pat. No. 7,570,358), which is incorporated herein by reference in its entirety.

FIELD

The present invention relates to methods of inspection usable, for example, in the manufacture of devices by lithographic techniques and to methods of manufacturing devices using lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. including part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at once, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is desirable to measure parameters of the patterned substrate, for example the overlay error between successive layers formed in or on it. There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

Many types of metrology (inspection) devices produce results that are dependent on the wavelength of the radiation used, for example because layers on the substrate being inspected have wavelength dependent optical properties or because layer thicknesses or structural pitches differently diffract the radiation used. Thus inspection devices of various types use either multiple monochromatic sources (e.g. lasers) providing outputs of different wavelengths or broadband sources and selectively insertable filters to enable measurements at different wavelengths to be performed either simultaneously or selectively.

However, coupling multiple laser sources into a single optical system of an inspection device often requires expensive optical multiplexing and/or demultiplexing devices and may be sensitive to alignment of the sources and other optical components. Swapping filters into and out of the inspection beam can be time consuming, reducing throughput of the inspection device when multiple measurements at different wavelengths need to be made.

An ellipsometer using a broadband source and an acousto-optical filter for fast wavelength selection is disclosed in WO 95/17662.

SUMMARY

It is desirable to provide an inspection device that can make measurements at multiple different wavelengths and that does not suffer from disadvantages of the prior art.

According to an embodiment of the invention, there is provided an angularly resolved scatterometer configured to determine a value related to a parameter of a target pattern printed on a substrate by a lithographic process used to manufacture a device layer on a substrate, the apparatus including a broadband radiation source arranged to emit a first beam of radiation having a first wavelength range; an acousto-optical tunable filter including an acousto-optical crystal arranged to receive the first beam of radiation, a transducer coupled to the acousto-optical filter and arranged to excite acoustic waves therein and a beam selecting device arranged to select as an output beam one of a plurality of beams output by the acousto-optical crystal in response to the first beam and the acoustic waves as a second beam of radiation having a second wavelength range, the second wavelength range being narrower than the first wavelength range; an optical system including a high-NA objective lens arranged to direct the second beam of radiation on to the target pattern and to project radiation reflected or scattered by the target pattern onto a detector to obtain a scatterometric spectra; and a driver circuit electrically coupled to the transducer and arranged to generate a drive signal therefor, the driver circuit being adapted to control the frequency of the drive signal so as to control the second wavelength range.

According to an embodiment of the invention, there is provided an inspection method to determine a value related to a parameter of a target pattern printed on a substrate by a lithographic process used to manufacture a device layer on a substrate, the method including using a broadband radiation source to emit a first beam of radiation having a first wavelength range; directing the first beam of radiation to an acousto-optical tunable filter including an acousto-optical crystal arranged to receive the first beam of radiation, a transducer coupled to the acousto-optical filter and arranged to excite acoustic waves therein and a beam selecting device arranged to select as an output beam one of a plurality of beams output by the acousto-optical crystal in response to the first beam and the acoustic waves as a second beam of radiation having a second wavelength range, the second wavelength range being narrower than the first wavelength range; using an optical system including a high-NA objective lens to direct the second beam of radiation on to the target pattern and to project radiation reflected or scattered by the target pattern onto a detector to obtain a scatterometric spectra; and providing a drive signal to the transducer, the drive signal having a frequency determined to control the second wavelength range.

According to an embodiment of the invention, there is provided an alignment sensor configured to determine a position of a target pattern printed on a substrate by a lithographic process used to manufacture a device layer on a substrate, the sensor including a broadband radiation source arranged to emit a first beam of radiation having a first wavelength range; an acousto-optical tunable filter including an acousto-optical crystal arranged to receive the first beam of radiation, a transducer coupled to the acousto-optical filter and arranged to excite acoustic waves therein and a beam selecting device arranged to select as an output beam one of a plurality of beams output by the acousto-optical crystal in response to the first beam and the acoustic waves as a second beam of radiation having a second wavelength range, the second wavelength range being narrower than the first wavelength range; an optical system including a self-referencing interferometer and arranged to direct the second beam of radiation on to the target pattern and to project radiation reflected or scattered by the target pattern onto a detector; and a driver circuit electrically coupled to the transducer and arranged to generate a drive signal therefor, the driver circuit being adapted to control the frequency of the drive signal so as to control the second wavelength range.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
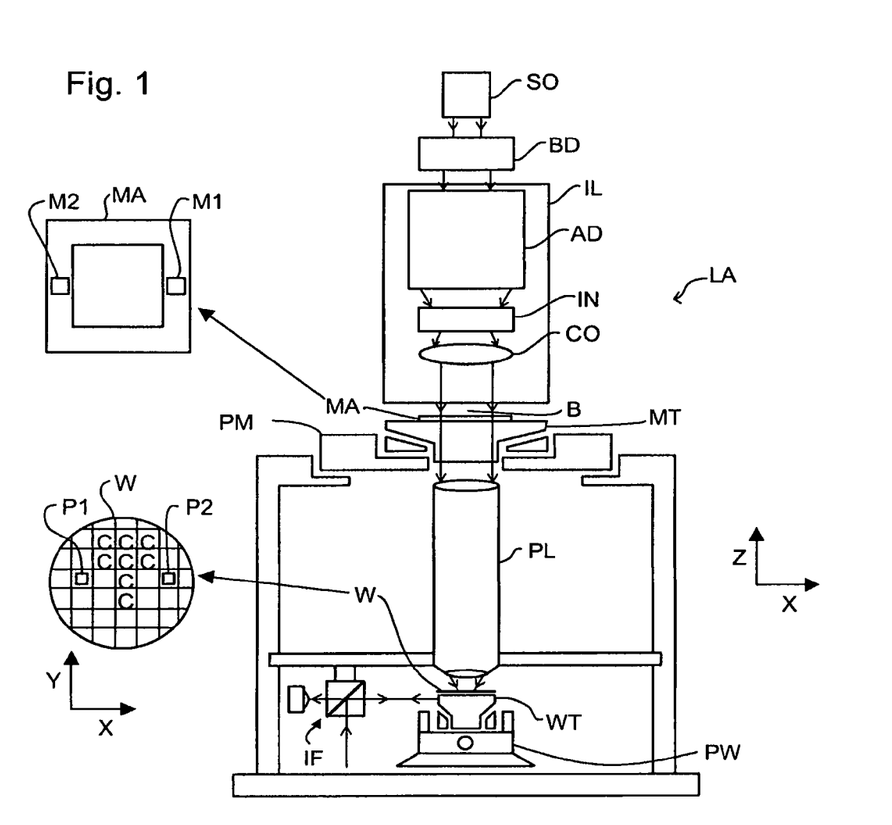
FIG. 1 depicts a lithographic apparatus in accordance with an embodiment of the invention.

FIG. 1 schematically depicts a lithographic apparatus. The apparatus includes an illumination system (illuminator) IL configured to condition a radiation beam B (e.g. UV radiation or DUV radiation) a support structure (e.g. a mask table) MT constructed to support a patterning device (e.g. a mask) MA and connected to a first positioner PM configured to accurately position the patterning device in accordance with certain parameters; a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PL configured to project a pattern imparted to the radiation beam B by patterning device MA onto a target portion C (e.g. including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the support structure (e.g., mask table) MT, and is patterned by the patterning device. Having traversed the patterning device (e.g. mask) MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the patterning device (e.g. mask) MA with respect to the path of the radiation beam B, e.g. after mechanical retrieval from a mask library, or during a scan. In general, movement of the support structure (e.g. mask table) MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure (e.g. mask table) MT may be connected to a short-stroke actuator only, or may be fixed. Patterning device (e.g. mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the support structure (e.g. mask table or pattern support) MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure (e.g. mask table) MT and the substrate table WT are scanned synchronously while a pattern imparted to the radiation beam is projected onto a target portion C (i.e. a single dynamic exposure). The velocity and direction of the substrate table WT relative to the support structure (e.g. mask table) MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the support structure (e.g. mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
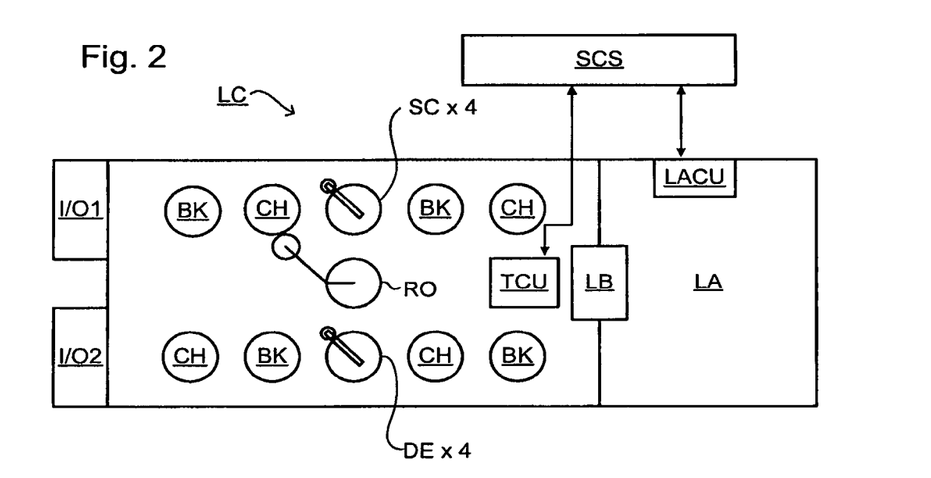
FIG. 2 depicts a lithographic cell or cluster in accordance with an embodiment of the invention.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded—thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
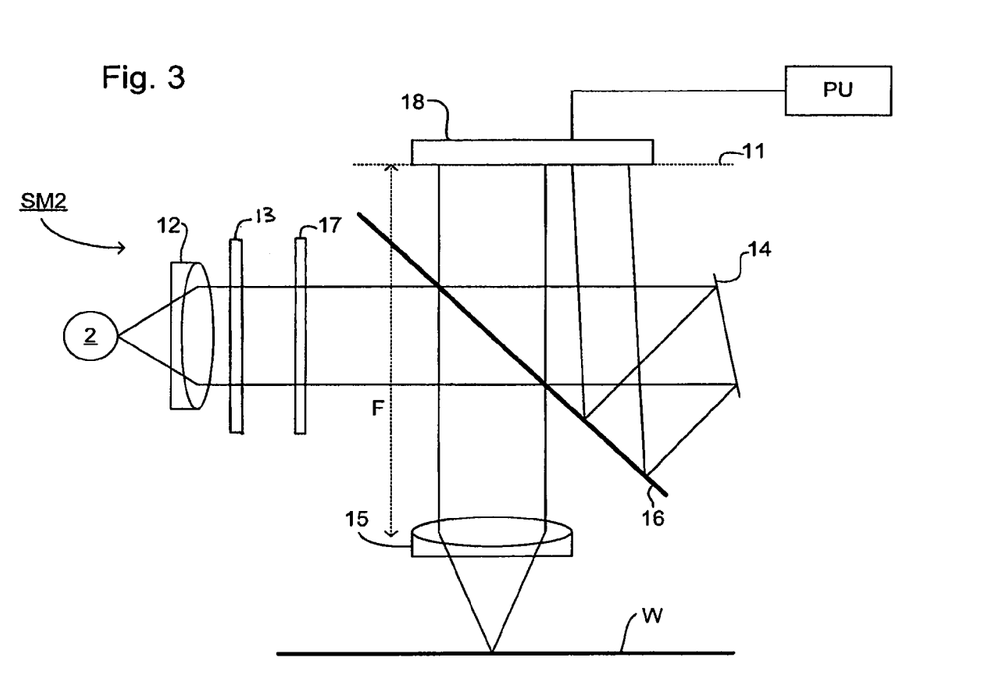
FIG. 3 depicts a scatterometer according to an embodiment of the invention.

A scatterometer SM2 according to an embodiment of the present invention is shown in FIG. 3. In this device, the radiation emitted by radiation source unit 2 (described further below) is focused using lens system 12 through polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is a plane in which the radial position of radiation defines the angle of incidence and the angular position defines azimuth angle of the radiation. The detector is preferably a two-dimensional detector so that a two-dimensional angular scatter spectrum of the substrate target can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

The target on substrate W may be a grating, which is printed such that after development, the bars are formed of solid resist lines. The bars may alternatively be etched into the substrate. This pattern can, for example, be made sensitive to aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU, from knowledge of the printing step and/or other scatterometry processes. Other forms of target may be used to measure other parameters of structures on the substrate or the processes used to produce them.

Figure 4:
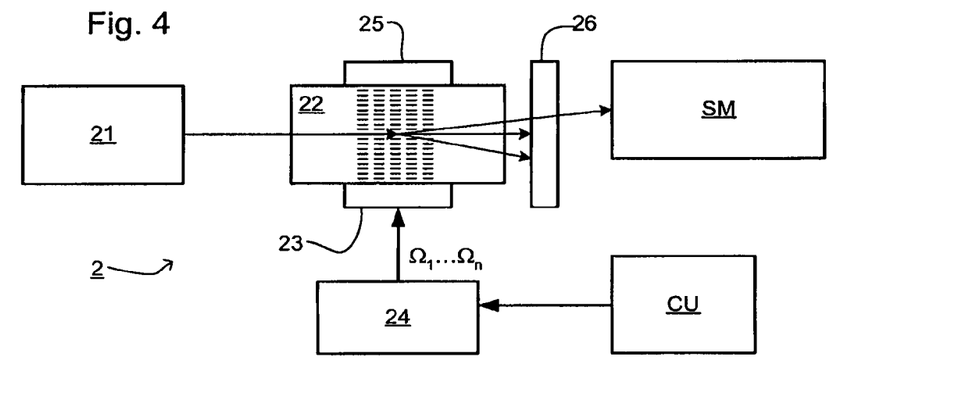
FIG. 4 depicts source and filter arrangements of the scatterometer of FIG. 2.

The radiation source unit 2 is shown in more detail in FIG. 4. The source includes a broadband source 21, such as for example a xenon lamp or a supercontinuum laser, which directs light into an acousto-optical tunable filter (AOTF) which is used to select a narrow range of wavelengths from the broadband (white light) output of the source 21 to form the inspection beam in the remainder of the scatterometer, depicted SM in FIG. 4.

The acousto-optical tunable filter (AOTF) includes an acousto-optical crystal 22 to which are connected a piezo-electric transducer 23, driven by a high-frequency driver circuit 24, and an acoustic absorber 25. Transducer 23 creates acoustic waves in the crystal 22 with a wavelength determined by the mechanical properties (speed of sound) of the crystal and driving frequencies. As these waves propagate through the crystal they form a periodic redistribution of the refractive index of the crystal due to the alternating expansion and contraction of the crystal lattice. This forms a diffraction grating which diffracts the light passing through it, although diffraction occurs throughout the region of interaction rather than at a single point and only radiation meeting phase and/or momentum matching conditions is diffracted. The net effect is that radiation of a narrow band of wavelengths is diffracted away from the main beam and can be selected by a spatial and/or polarizing filter 26. The center wavelength of the diffracted beam is dependent on the driving frequency of the transducer so it can be controlled within quite a wide range and very rapidly, dependent on the response time of the driver circuit 25, the transducer and the crystal. The intensity of the diffracted beam is also controlled by the intensity of the acoustic waves.

Suitable materials which can be used for the acousto-optical crystal include: Quartz ($SiO2$), KDP ($KH_2PO_4$), Paratellurite or tellurium dioxide ($TeO_2$), LiNbO3, calomel or mercuric chloride ($Hg_2Cl_2$), TAS ($Ta_3AsSe_3$) and Te (tellurium), magnesium fluoride (MgF), and sapphire (aluminum oxide, $Al_2O_3$). The crystal selected determines the detailed geometry of the acousto-optical tunable filter. If a birefringent crystal is used, the filter may also select a particular polarization state.

High frequency drive unit 24 is connected to the control unit CU of the scatterometer which provides a drive signal to cause the transducer to emit acoustic waves of an appropriate frequency to select a narrow band of wavelengths centered on a desired wavelength, as required for a given measurement. The bandwidth of the transmitted beam is preferably less that about 20 nm, less than about 15 nm, less than about 10 nm or less than about 5 nm. The exact relationship between frequency of drive signal and selected wavelength depends on the particular crystal employed and the geometry of the device. In some cases, by applying a drive signal having two or more components of different frequencies $\Omega_1$ to $\Omega_n$, the filter can be operated to select a plurality of components each centered around a different wavelength, which forms a polychromatic beam that allows a plurality of measurements to be made simultaneously. The intensities of the different frequency components of the drive signal can be varied to individually control the intensities of the different wavelengths in the polychromatic beam.

Figure 5:
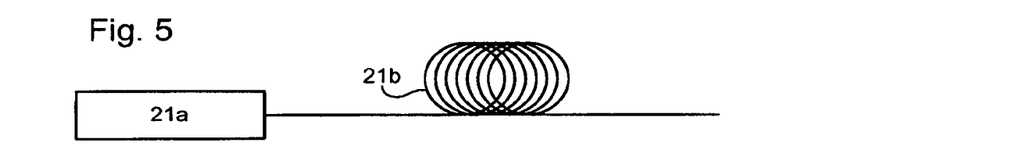
FIG. 5 depicts a super-continuum laser source usable in embodiments of the invention.

An beneficial light source that can be used in an embodiment of the present invention is a supercontinuum laser, which is illustrated in FIG. 5. This source includes a pulsed laser source 21a whose output is fed into a non-linear medium 21b, e.g. a photonic crystal fiber. The pulsed source 21a emits very short pulses, e.g. of femtosecond or picosecond duration, of a narrow band of wavelengths which are spread by the non-linear medium 21b into a broadband beam of radiation. This type of source can provide a powerful beam with a low etendue and a suitable range of wavelengths.

Figure 6:
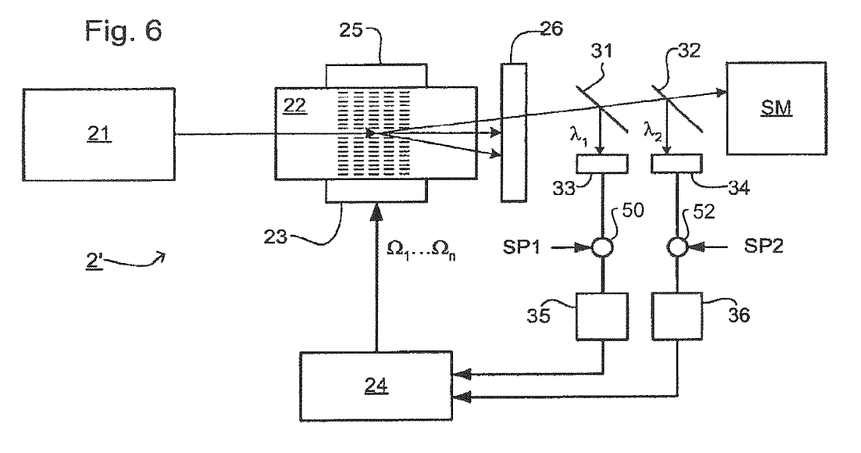
FIG. 6 depicts source and filter arrangements of another scatterometer according to an embodiment of the invention.

An additional benefit of the use of an acousto-optical tunable filter is that, due to its fast response time, it can be used to reduce noise in the measurement beam, especially when a supercontinuum laser is used as the light source. An embodiment of the invention employing this benefit is shown in FIG. 6 and is the same as the embodiment as described below.

In this embodiment of the radiation source unit 2', after the spatial or polarizing filter 26, dichroic beamsplitters 31, 32 are positioned in the beam path. Each dichroic beamsplitter diverts a predetermined proportion of one component of the output beam of the acousto-optical tunable filter to a respective detector 33, 34 which measures the intensity of the diverted radiation. The measured intensity value is compared to a respective setpoint SP1, SP2 using respective comparators 50, 52 and the difference (error) is provided to a respective controller 35, 36, e.g. a proportional-integral-derivative controller (PID controller), which provides a control signal to the driver 24 to control the amplitude of the relevant frequency component $\Omega_1$ to $\Omega_n$ in the drive signal to the transducer 23. The response time of the control loop 24, 23, 22, 33/34, 35/36 can be of the order of microseconds, e.g. 10 μs, 5 μs or 2 μs, so allowing reduction of noise of frequency up to about 40 kHz, which is very useful. Although two control loops are shown, more than two may be provided, each controlling an output beam of different wavelength. It should be noted that if the noise in the beam output by the radiation source 21 is relatively constant over a wavelength range encompassing several different components of the output beam, one control loop may be used to control the amplitude of more than one frequency component in the drive signal. In the limit, a single control loop may control the amplitude of all frequency components of the drive signal and hence the intensities of all components of the output beam.

Figure 7:
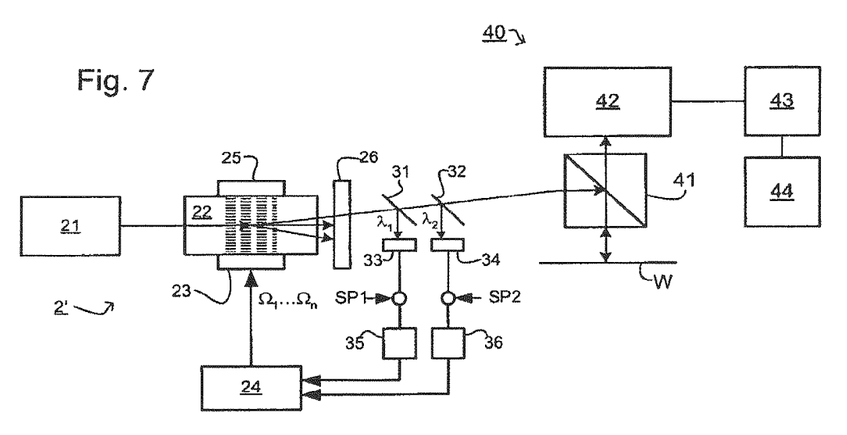
FIG. 7 depicts an inspection apparatus according to another embodiment of the invention.

Another embodiment of the invention is depicted in FIG. 7. This includes an alignment system 40 of the type described in EP-A-1,148,390, which document is hereby incorporated by reference, and uses a compact self-referencing interferometer 42 and a beam splitter 41 to generate two overlapping images of a target on substrate W, rotated over +90° and −90°, which are then made to interfere in a pupil plane. An optical system and spatial filter selects and separates the first order beams and re-images them on a detector 43 whose output is processed by a signal analyzer 44 to provide the required measurement. In a variant of this type of metrology device which can also be employed in the present invention, the detector can be placed in the pupil plane. Further details are given in EP-A-1 372 040, which document is hereby incorporated by reference. The light source 2', which is the same as the light source 2' described above, is used to provide a beam of radiation of the desired wavelength or wavelengths that has a stable intensity and reduced noise, which is ideal for this type of alignment sensor.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. An angularly resolved scatterometer, comprising:
    an acousto-optical tunable filter configured to receive an input beam of radiation from a radiation source configured to produce the input beam with a first wavelength and to produce an output beam therefrom;
    an optical system comprising a lens configured to direct the output beam to a target pattern and to project radiation reflected or scattered by the target pattern onto a detector; and
    a beam splitter configured to divert a portion of the output beam to the detector,
    wherein the detector is configured to detect an intensity of the diverted portion and to generate a corresponding intensity measurement signal fed to a driver electrically coupled to the acousto-optical tunable filter and configured to control a driver signal based upon the intensity measurement signal.

2. The angularly resolved scatterometer of claim 1, wherein the driver signal adjusts an amplitude of the output beam.

3. The angularly resolved spectrometer of claim 1, wherein the acousto-optical tunable filter comprises:
- an acousto-optical crystal configured to receive the input beam;
- a transducer coupled to the acousto-optical filter and configured to excite acoustic waves in the acousto-optical crystal; and
- a beam selecting device arranged to select as the output beam one of a plurality of beams, output by the acousto-optical crystal in response to the input beam and the acoustic waves, having a second wavelength, the second wavelength being narrower than the first wavelength.

4. The angularly resolved spectrometer of claim 3, wherein the beam selecting device is a polarizing filter.

5. The angularly resolved spectrometer of claim 3, wherein the beam selecting device is a spatial filter.

6. The angularly resolved spectrometer of claim 1, wherein the detector, the beam splitter and the driver comprise a feedback loop.

7. The angularly resolved spectrometer of claim 6, wherein the feedback loop comprises a comparator coupled to the detector and the driver.

8. The angularly resolved spectrometer of claim 1, wherein the target pattern is a grating on a silicon substrate.

9. The angularly resolved spectrometer of claim 1, wherein the acousto-optical tunable filter is configured to select a plurality of beams that are centered around different wavelengths, based on the driver signal that includes two or more components of different frequencies, to form a polychromatic beam that allows a plurality of measurements to be made simultaneously.

10. The angularly resolved scatterometer of claim 1, wherein:
- the driver is configured to generate a drive signal having a plurality of different frequency components; and
- the acousto-optical tunable filter is configured to output substantially simultaneously a plurality of second beams of radiation having respectively different wavelength ranges.

11. The angularly resolved scatterometer of claim 10, wherein the beam splitter is a dichroic beam splitter that is configured to divert a predetermined portion of a respective one of the plurality of second beams of radiation to the detector.

12. The angularly resolved scatterometer of claim 10, further comprising:
- a plurality of detectors; and
- a plurality of dichroic beam splitters each arranged to divert a predetermined portion of a respective one of the plurality of second beams of radiation to a respective one of the detectors;
- wherein each of the detectors is arranged to detect an intensity of the diverted portion of the respective one of the plurality of second beams and to generate a respective intensity measurement signal,
- wherein the driver controls an amplitude of the respective frequency component of the drive signal based on the intensity measurement signal and thereby controls the amplitude of the respective one of the plurality of second beams of radiation.

* * * * *